United States Patent [19]

Benz et al.

[11] Patent Number: 5,292,638
[45] Date of Patent: Mar. 8, 1994

[54] METHOD OF DETERMINING FUNCTIONAL ESTROGEN RECEPTORS FOR PROGNOSIS OF CANCER

[75] Inventors: Christopher C. Benz, Novato; Gary K. Scott, Berkeley, both of Calif.

[73] Assignee: The Regents of the University of California, Oakland, Calif.

[21] Appl. No.: 623,607

[22] Filed: Dec. 7, 1990

[51] Int. Cl.$^5$ .................. C12Q 1/68; G01N 33/574; G01N 33/561
[52] U.S. Cl. .................. 435/6; 435/7.1; 435/7.21; 435/7.23; 435/962; 436/501; 436/504; 436/514; 436/516; 436/63; 436/64; 436/813; 436/824; 204/182.8
[58] Field of Search ............ 435/6, 7.1, 7.2, 7.23, 435/803, 962; 436/501, 504, 514, 516, 63, 64, 813, 824; 204/180.1, 182.8

[56] References Cited

PUBLICATIONS

Klein-Hitpass, L., et al., *Mol. Cell. Biol.*, vol. 9, No. 1, pp. 43–49 (Jan. 1989).
Murdoch, F. E., et al., *Biochemistry*, vol. 29, pp. 8377–8385 (Sep. 1990).
Peale, F. V., et al., *Biochemistry*, vol. 28, No. 22, pp. 8671–8675 (Oct. 31, 1989).
Hoehn, J. L., et al., Biological Abstracts, vol. 69, No. 3, The Abstract No. 18110, (Feb. 1980).
C. C. Benz, G. K. Scott, Abstract: *Can. Gel-shift Assays Detect Hormone Resistant ER-Positive Breast Cancers?*, Breast Cancer Res. Treat., 14:178 (1989), Editor W. L. McGuire, Kluwer Academic Publishers.
V. Kumar, P. Chambron, *The Estrogen Receptor Binds Tightly to its Responsive Element as a Ligand-Induced Homodimer Cell*, 55:145 (1988).
F. Keeman, UCSF Specialist Questions Therapy for Breast Cancer, *San Francisco Examiner*, A-16 Tuesday, Mar. 27, 1990.
Associated Press, Soybeans May Prevent Breast Cancer, A5, *Marin Independent Journal*, Tuesday, Mar. 27, 1990.
R. Knox, Odds of Breast Cancer Relapse May be Misstated, Scientist Says, *Boston Globe*, Mar. 26, 1990.
T. Friend, Other Promising Research, *USA Today-Life*, Mar. 27, 1990.
G. Scott, P. Kushner, J. L. Vigne, and C. Benz, J. Clin. Invest., *Truncated Forms of DNA-binding Estrogen Receptors in Human Breast Cancer*, Journal of Clinical Investigation, Inc., vol. 88, 700–706, (Aug. 1991).

*Primary Examiner*—Esther L. Kepplinger
*Assistant Examiner*—Toni R. Scheiner
*Attorney, Agent, or Firm*—Hana Dolezalova

[57] ABSTRACT

A method and assay for determination of functionality of steroid receptors present in breast or other tumors. The method is useful for determination of cancer responsiveness to hormonal therapy by establishing a correlation between functioning estrogen receptors and those which are dysfunctional or nonfunctional. The assay is useful for determination whether the cancer, particularly the breast cancer, will respond to antiestrogen hormonal therapy.

6 Claims, 3 Drawing Sheets

FIGURE 2A
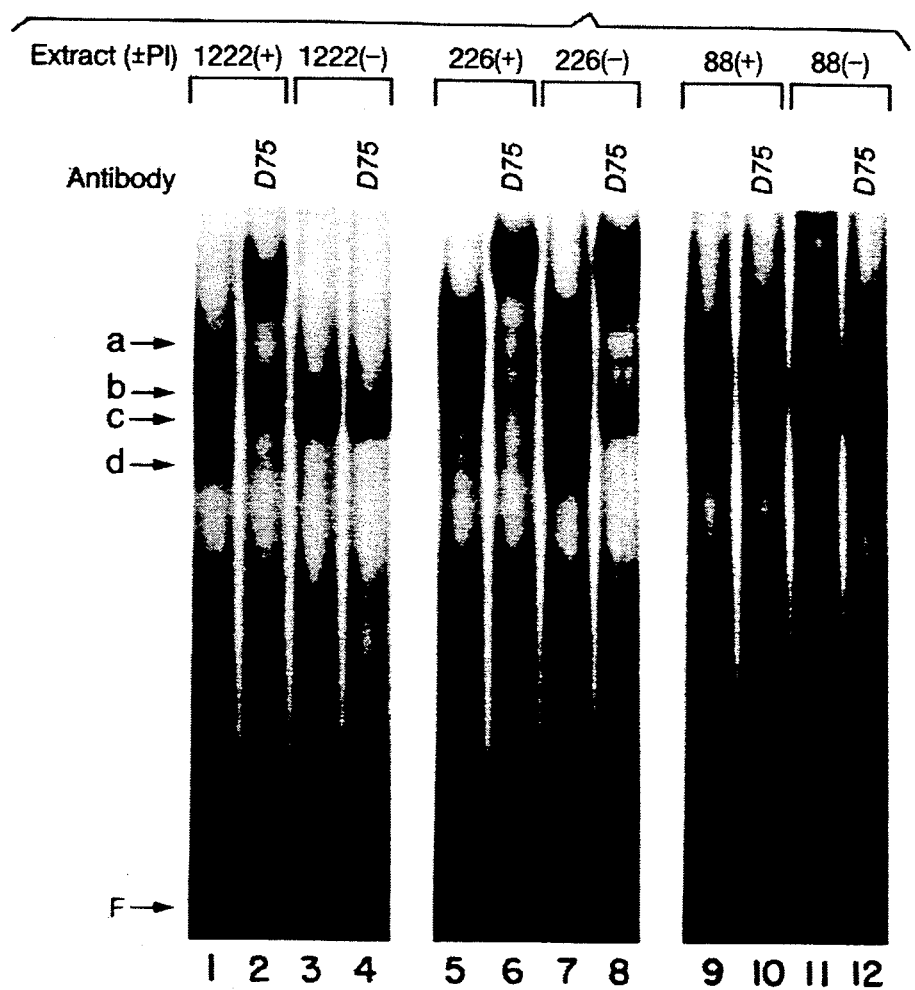
FIGURE 2B
FIGURE 2C
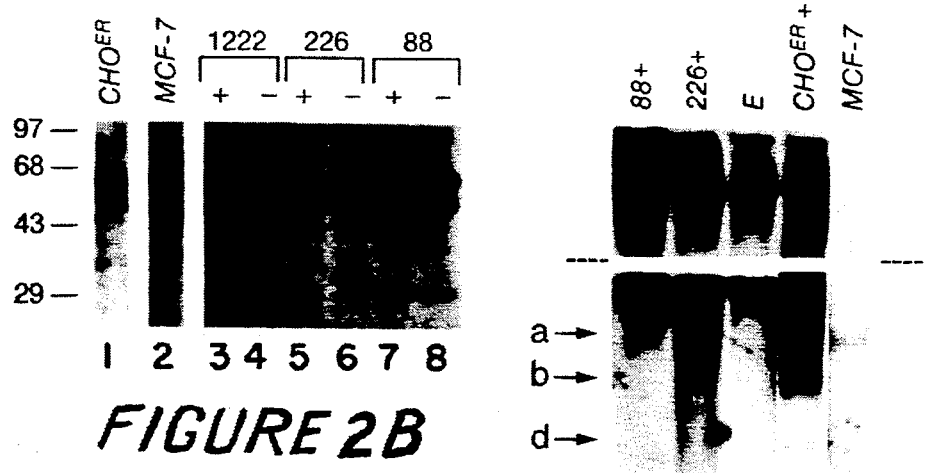

METHOD OF DETERMINING FUNCTIONAL ESTROGEN RECEPTORS FOR PROGNOSIS OF CANCER

This invention was made with Government support under Grant Nos. CA-36773 and CA-44768 awarded by the National Institute of Health. The Government has certain rights in this invention.

BACKGROUND OF THE INVENTION

1. Field of Invention

This invention concerns a new and effective method and assay for determination of functionality of steroid receptors present in breast or other tumors. The method determines cancer responsiveness to hormonal therapy by measuring the level of DNA-binding (functioning) and non-DNA binding (nonfunctioning) steroid receptors and establishing a correlation between such functioning estrogen receptors and those which are dysfunctional or nonfunctional. In particular, this method distinguishes and quantifies steroid receptors capable of binding to DNA from those which do not bind to DNA or bind abnormally. The two-step gel-shift Western blot assay is useful for determination whether the cancer, particularly the breast cancer, will respond to antiestrogen hormonal therapy.

2. Background Art and Related Disclosures

Breast, uterine or prostate cancers are among the most serious cancerous diseases. Breast carcinoma is one of the most common malignancy among women and has the one of the highest fatality rate of all cancers affecting this sex. American Cancer Society estimates that around 44,000 U.S. women die from breast cancer each year.

Treatment of the breast, ovarian, uterine or prostate cancer may be either palliative or curative. The choice of treatment depends mainly on the extent of the disease. When the cancer is localized primarily in the breast, ovarian, uterine or prostate tissue, treatment by surgery is usually the first choice therapy. Radiotherapy, hormonal therapy, cytotoxic chemotherapy and to a lesser degree immunotherapy are used for both the palliative treatment or as adjuvants to surgery. Both radiotherapy and chemotherapy are accompanied by many unpleasant, undesirable and dangerous side effects. Immunotherapy is still in its experimental stage.

For the past 15 years, hormonal therapy had been shown to be effective, to a certain degree, for breast, uterine or for prostate cancer treatment. Hormonal therapy is typically used in palliation of symptoms or in delaying advance of the disease. Hormonal therapy utilizes analoques of both androgens and estrogens, however, in patients having postmenopausal or recurrent breast cancer, estrogen-based treatment is preferred.

In recent years, in pursuance of research related to breast cancer and its treatment, the presence of so called estrogen-receptors (ER) and progesterone-receptors (PR) was discovered in certain breast tumors. Currently, it is believed that women whose breast cancer cells contain estrogen and/or progesterone receptors have a much better chance to survive if they are treated with estrogen blocking drugs such as Tamoxifen, a non-steroidal estrogen antagonist.

The presence or absence of estrogen and progesterone-receptor protein in primary or metastatic tumor tissue is used nowadays to predict which patient may be expected to respond to additive or ablative endocrine therapy. The presence of ER is correlated with expected responsivity of the cancer to the hormonal therapy. The absence of ER is correlated with expected nonresponsiveness to the hormonal therapy. Notwithstanding, some 20-70% of tumors containing estrogen receptors (ER) fail to respond to hormone therapy. This leads to a belief that some of these estrogen receptors may be nonfunctional or dysfunctional in some way. Since the untreated breast cancer is a fatal disease, such non-responsiveness to the hormonal therapy due to the estrogen receptors dysfunctionality has very serious consequences. Patients with tumors known to contain abnormal ER where the probability of the cancer responsiveness to hormonal treatment is low would be offered other forms of therapy instead of hormonal therapy.

It would, therefore, be of a great prognostic value and therapeutic importance to have available a method and assay for determination whether the estrogen receptors are functioning, what is the correlation of the functional to nonfunctional receptors and to predict from such determination whether the particular cancer cells containing estrogen receptors will respond to a hormonal therapy.

Estrogen receptors belong to a family of nuclear receptors whose function is dependent on the binding of small hydrophobic ligands. In the estrogen receptor case, it depends on the binding of the hormone estradiol. The binding of estrogen receptors (ER) to its estrogen responsive element (ERE) has been described in *Cell*, 55:145 (1988). Estradiol or the anti-estrogen hydroxytamoxifen were shown to be necessary for the estrogen receptor binding to its ERE binding domain on DNA.

Gene transfer studies have shown that estrogen regulation of specific genes is mediated by ERE. This binding interaction is highly sequence and receptor specific. Estrogen receptor seems to bind to the ERE as a head-to-head dimer. The binding of estrogen receptor to the ERE is detectable by a gel retardation (band shift) assay. Such assay, utilizing ERE of the vitellogenin A2 gene for specific estrogen receptor binding, is described in *Cel. Biol.*, 9:43 (1989). The presence of estrogen receptors in the receptor protein-DNA complexes is measured by mobility shift of the protein-DNA complexes. The specificity of the ERE for estrogen receptor is evidenced by the lack of estrogen binding to a progesterone response elements (PRE).

The first modifications to a basic gel-shift assay described above were disclosed by inventors during the 12th Annual San Antonio Breast Cancer Symposium, held on Dec. 8-9, 1989, and are briefly and incompletely described in the Proceedings Abstracts, published in *Breast Cancer Res. Treat.*, 14:178 (1989). The modified gel-shift assay determines the formation of ER-ERE complexes as a measure of ER activation and functionality which is necessary for a responsiveness of the breast cancer to hormonal treatments.

Previously used receptor assay techniques were directed only toward a determination of the presence or the absence of ER and its quantification but not to the activation and functionality of ER which is believed to be necessary for both high-affinity DNA (ERE) binding and for a transcriptional control. The presence of ER in the breast cancer cells that is unable to bind to ERE, or binds to ERE in an improper form may thus explain prior clinical findings of ER-positive and yet hormone resistant breast cancers.

The primary feature of this invention is thus directed toward a method and ultimately toward an assay which measures both the ability to form ER-ERE complexes and the amount of ER that is unable to bind ERE, both of which determine ER functionality. Ultimately, the utility of this invention lies in a determination whether breast cancer will respond to hormonal treatment or not.

The one-step gel-shift DNA binding receptor assay suitable to distinguish between functional and nonfunctional ER-ERE isoforms is disclosed herein as one novel feature of this invention. The second feature of this invention is directed toward a two-step gel-shift Western blot assay which can distinguish and quantify functioning steroid receptors present in human tissue i.e., distinguish those receptors which are capable of binding normally or abnormally to DNA by gel-shift assay, from those receptors which are nonfunctional, i.e. which fail to bind to DNA (ERE) completely. For this purpose, the new two-step gel-shift Western blot assay for detection and quantitation of non-DNA binding steroid receptors has been developed and is disclosed herein as yet another novel feature of this invention.

SUMMARY

One aspect of this invention concerns a new method for determination of responsiveness of cancer, particularly uterine, ovarian, prostate or breast cancers, to hormonal treatment.

Other aspect of this invention is measurement of DNA-binding and non-binding steroid receptors and determine the correlation as prognostic cancer indicator.

Another aspect of this invention concerns a method wherein by measuring DNA-binding and non-binding steroid receptors in a tumor sample, a correlation is established between functional estrogen receptors binding to the ERE and forming normal ER-ERE complexes and isoforms, and a method wherein by establishing in a breast tumor sample a correlation between steroid receptors binding to the DNA (ERE), forming ER-ERE complexes, and nonfunctional ER that is not capable forming any ER-ERE isoforms, dysfunctional or nonfunctional ER forming abnormal ER-ERE isoforms, on the basis of which correlation a responsiveness of the cancer to hormonal treatment will be predicted.

Another aspect of this invention concerns responsiveness of breast cancer to hormonal treatment will be predicted.

Still yet another aspect of this invention concerns an improved one-step gel-shift assay where the ER-ERE complexes are formed and separated by gel-electrophoresis into their specific isoforms from both the unbound ER and unbound DNA.

Still another aspect of this invention concerns a new two-step gel-shift Western blot assay useful for the direct measurement of free DNA-unbound ER and for determination of qualitative and quantitative presence of ER-ERE isoforms.

BRIEF DESCRIPTION OF FIGURES

FIGS. 2A, 2B and 2C depicts DNA binding and nonbinding immunoreactive ER from representative breast tumor samples (2A), composition of total immunoreactive ER (2B) and the amount of non-DNA binding ER as measured by the gel-shift Western blot (2C).

DETAILED DESCRIPTION OF THE INVENTION

Definitions

Figure 1A:
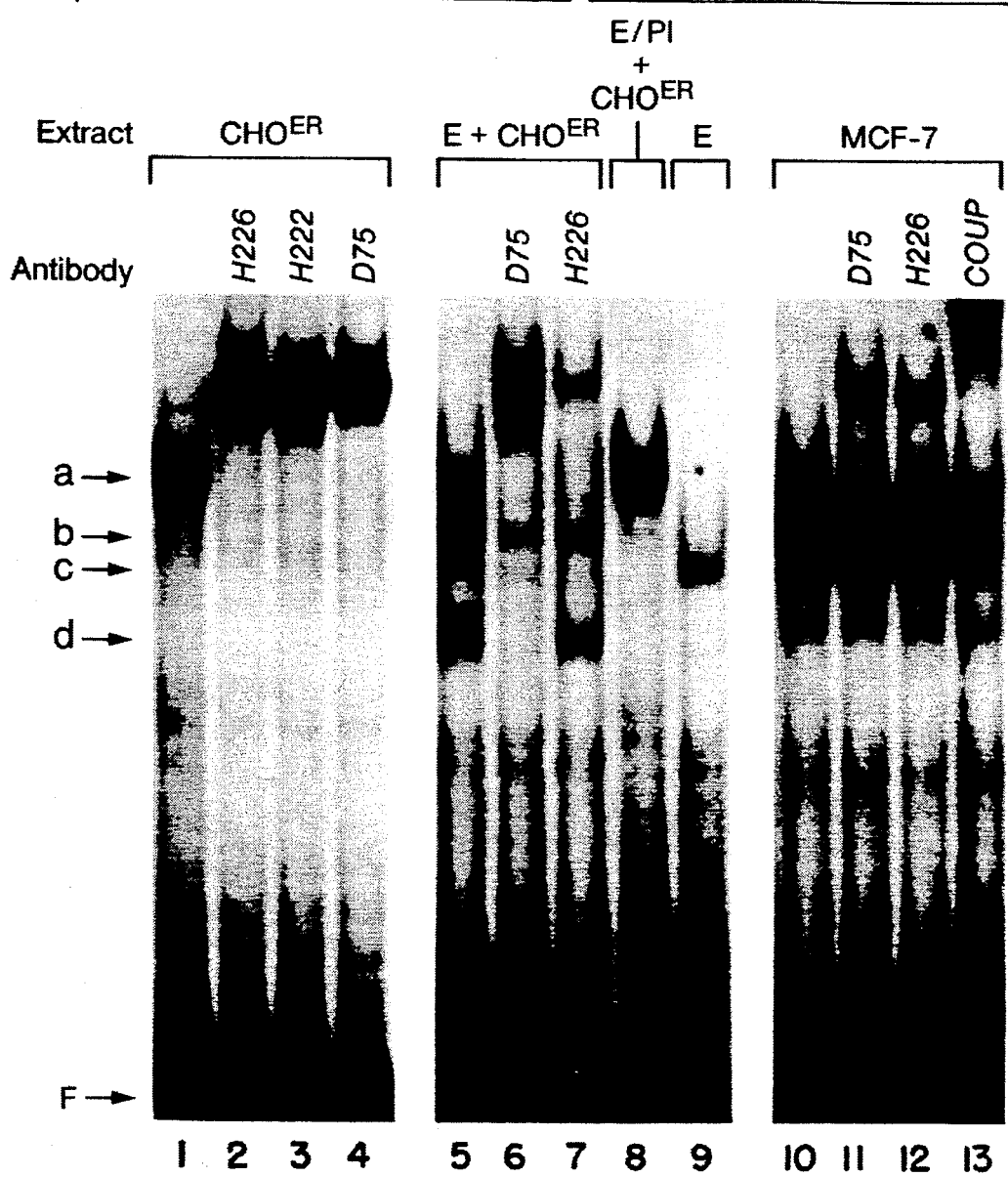
FIGS. 1A and 1B depict detection (1A) and composition (1B) of DNA binding estrogen receptor (ER-ERE) isoforms.

As used herein:

"ER" means estrogen receptor.

"ERE" means estrogen responsive element.

"COUP" means an ERE-binding transcriptional factor which possesses near equivalent ERE binding affinity and specifity to those of ER, thyroid hormone receptors (THR) and retinoic acid receptors (RAR) and which is found to be present in human tissue.

"Steroid receptor" means and encompasses receptors such as estrogen, progesterone, androgen, glucocorticoid, thyroid hormone and retinoic acid receptors.

"Functionality" of steroid receptor means the determination of competence of the steroid receptor to bind to its unique target gene DNA, steroid response element, such as ERE or estrogen response element. The receptor is functional when it binds to DNA and nonfunctional when it does not bind or binds abnormally. Nonfunctional or dysfunctional receptors point toward low responsiveness of a tumor to the hormonal treatment. The functional receptor points toward responsiveness of the tumor to the hormonal treatment.

"Tumor responsiveness" means the propensity of the tumor to respond to appropriate hormonal treatment.

"Isoforms" means gel-shifted DNA ER-ERE complexes which are distinguishable after autoradiography or some other such separation technique which isoforms are herein designated a, b, c, d and X but are intended to encompass all other isoforms which may be found and present in tumor cells as ER-ERE complexes.

DESCRIPTION OF THE INVENTION

This invention concerns a new method f or determination of whether a particular cancer will or will not respond to a hormone therapy. The ultimate result of this method is a development of a new assay, consisting of two steps which, combined, provide fast and effective test for determination and prediction whether the hormonal treatment is the appropriate therapy for the particular cancer.

It has been previously determined that the measurement of steroid receptors, especially estrogen receptors (ER) and progesterone receptors (PR) from human tissue samples provides clinically essential prognostic and therapeutic information that is most important in the evaluation of various human tumors derived from breast, ovarian, uterine, and even prostate tissue.

Existing commercialized receptor assays simply measure the tissue content, i.e., level of steroid receptors but do not determine DNA binding and functional competency of these receptors. Yet, only functionally competent, DNA binding receptors account for the clinical response of importance. Thus, current measurements of receptor levels lead to imprecise clinical decisions in 20%–70% of patients by improperly predicting a response of these patients to the hormonal treatment. Consequences of such improper treatment decisions may be serious or even fatal for a patient. Moreover, these decisions also may cause unnecessary treatment expenses.

This invention is based on critical modifications to a basic gel-shift assays currently used, which modifications allow routine measurement of DNA-bound ER presence in human biopsy materials.

Using these newly developed techniques, the new observations were made that previously unknown various DNA binding ER isoforms a, b, c and d of steroid receptors appear to exist in similar tumor specimens, such as in ER or ER/PR positive breast cancers, introducing the possibility that each isoform within a given tumor may be useful for prediction of a specific prognosis and therapeutic response of that tumor.

Many ER-positive breast tumor samples were found to contain an enzymatic activity that reduces the amount of isoform a derived from intact human ER. These tumors produce, instead, two additional bands of increased gel mobility, namely isoforms b and d. Such conversion of isoform a to isoforms b and d is shown in FIG. 1A, lane 5, after co-incubation of CHO$^{ER}$ sample with a small amount of extract E, derived from the breast tumor. This conversion can be prevented by heat pretreatment of E or by co-incubation of tumor extract with protease inhibitors (PI) such as leupeptin, or other thiol and/or serine protease inhibitors but not by phosphatase inhibitors such as molybdate, vanadate, etc.

The new gel-shift DNA binding receptor assay is based on the in vivo requirement that each steroid receptor binds to its unique target gene DNA sequence. Even a single base alteration in this DNA sequence, as would appear to be present in each isoform if correctly chosen, eliminates the specificity of binding between the different isoform of the steroid receptor, that is between ER and its DNA response element.

Similar but very simple gel-shift assays for ER-ERE complex formation have been recently described in *Mol. Cel. Biol.*, 9:43 (1989). The investigators however, used model non-specimen systems and technical conditions that do not allow their methods to be directly applied to the analysis of clinical tissue specimens such as human tumors or biopsy material. Also, since the described assay does not separate ER-ERE complexes into isoforms, the existence of various DNA-binding steroid receptor isoforms currently discovered in human tissues was not recognized.

By substantially changing the assay conditions such as by adding excess amounts of non-specific DNA sequences and subtracting out the amount of receptor that can non-specifically bind to a mutant response element that differs by the exchange of two critical bases in its dyad symmetry unit and by adding anti-ER antibody which cause a supershift of ER-ERE complexes and separate them from other ERE binding complexes like COUP-ERE, THR-ERE and RAR-ERE, it was shown by the new gel-shift technique of this invention that at least four but probably more different ER DNA-binding receptor isoforms can exist in tissues with measurable steroid receptor levels.

Furthermore, in tumor tissues with very high receptor levels, DNA binding isoforms are often not detectable thus signifying the abundant presence of non-functional or abnormal receptors. Such very high level of nonfunctional receptors would point toward low responsiveness or resistance of the tumor to all forms of hormonal treatment that depends on that receptor.

These findings suggests that the new assay would be able to provide more informative clinical data and more precise prognostic and therapeutic information about each tissue or tumor sample being analyzed.

To test the above hypothesis, ER activation in breast cancer cells was studied by the novel, modified and improved gel-shift Western blot DNA binding receptor assay.

Since tumors with nonfunctioning and immunologically detectable ER will not have the same clinical behavior as tumors with functioning DNA binding estrogen receptor isoforms, and since currently available steroid receptor assays are unable to distinguish the normal DNA-binding from abnormal or non-DNA binding receptors, the previously available assays are not reliable prognostic tools in prediction of cancer's responsiveness to the hormonal treatment.

The novel assay of this invention, however, provides a means to distinguish between individual isoforms a, b and d and also to quantitate these isoforms. One tumor sample was found having a very large level of a novel isoform X. The one way to confirm the specificity of the receptor binding to DNA and an important means of identifying unambiguously the DNA-bound complexes, is the use of anti-ER antibodies which will bind to ER that is also bound to ERE, and causing a supershift in the isoforms a, b and d ER-ERE complexes. Preliminary findings on a variety of cryopreserved ER-positive breast cancer samples, as shown in Table 1, show the presence or absence of the intact isoform a.

Using this new technique, the partial or complete functionality of ER receptors in tissue samples shown in Table 1 was assessed.

TABLE 1

DNA BINDING ESTROGEN RECEPTOR IN HUMAN BREAST TUMORS

| Tumor Samples | Receptor Content (ER/PR)* | ER-ERE Isoform a |
|---|---|---|
| 87-165 | −/− | − |
| 88-172 | −/− | − |
| 88-244 | −/− | − |
| 88-263 | −/− | − |
| 88-277 | −/− | − |
| 87-287 | −/++ | − |
| 88-18 | +/− | − |
| 88-142 | +/− | + |
| 88-135 | +/− | − |
| 86-187 | +/− | + |
| 87-655 | +/? | + |
| 87-1222 | +/? | − |
| 88-2 | +/? | + |
| 87-240 | ++/− | − |
| 88-287 | ++/− | − |
| 88-246 | ++/? | − |
| 88-224 | +/+ | − |
| 89-88 | +/+ | − |
| 89-164 | +/+ | + |
| 89-192 | +/+ | − |
| 89-221 | +/+ | − |
| 89-183 | +/++ | − |
| 89-155 | +/++ | + |
| 86-14056 | ++/+ | + |
| 87-73 | ++/+ | + |
| 88-229 | ++/+ | + |
| 89-151 | ++/+ | − |
| 89-225 | ++/+ | + |
| 88-110 | ++/++ | + |
| 88-138 | ++/++ | + |
| 88-242 | ++/++ | − |
| 89-116 | ++/++ | − |
| 88-143 | ++/++ | + |
| 89-90 | ++/++ | + |

TABLE 1-continued

DNA BINDING ESTROGEN RECEPTOR IN HUMAN BREAST TUMORS

| Tumor Samples | Receptor Content (ER/PR)* | ER-ERE Isoform a |
|---|---|---|
| 89-226 | ++/++ | + |
| 89-294 | ++/++ | + |
| 90-6 | ++/++ | + |

*Receptor content of 0-19 (−), 20-99 (+), or ≧100 (++) fmol/mg protein cytosol; ? = not determined.
Isoform a = 0-49% (−) or 50-100% (+) of total antibody recognized DNA complexes (ER-ERE).

From the results summarized in Table 1, there seems to be a certain correlation between ER/PR presence or absence in tumor sample to the presence or absence of the intact ER-ERE isoform a. For example, in all tumors which were shown to be both ER and PR negative, no isoform a was present. In tumor samples which were ER positive and PR negative, there was a general lack of a isoform with only four of ten tumors having intact isoforms a. In the group of 21 samples which are both ER and PR positive, 13 samples contain predominantly the isoform a. In the remaining eight samples, isoforms b and d, were more abundant than isoform a or there were no DNA-binding isoforms at all.

In those tumors having negative isoform a, gel-shift Western technique demonstrates that the immunoreactive ER was non-DNA binding.

These observations have great significance for prognosis of the tumor responsiveness to the hormone treatment. In view of prior findings that loss or absence of isoform a in many ER-positive tumors signifies the presence of predominantly non-DNA binding ER, the chances are that the majority or all of the tumor ER are nonfunctional and consequently would not respond to the hormonal treatment. This is true particularly in the ER positive and PR negative group. On the other hand, if the isoform a is present in large levels with low or absent levels of non-DNA binding ER, the chances are substantially increased that the tumor will respond to hormonal treatment.

The presence of intact estrogen receptor DNA binding (isoform a) in tumor cells seems to be correlated with higher content of immunoreactive sex steroid receptors, particularly the estrogen and/or progesteron receptors. These receptors are considered to be standard indicators of tumor responsiveness to anti-estrogen. This correlation suggests that loss of estrogen receptor DNA binding is an important prognostic parameter accounting for some forms of clinical resistance to anti-estrogen therapy.

To assess the prevalence and potential clinical significance of tumors lacking intact DNA binding ER, total immunoreactive ER and PR content in all tumors analyzed by gel-shift assay were compared in Table 2.

TABLE 2

| Receptor | Content* | ER-ERA$_a$ | Complex# | |
|---|---|---|---|---|
| ER | − | 0/6 | (0%) | |
| | + | 6/14 | (43%) | P = 0.002 |
| | ++ | 12/18 | (67%) | |
| PR | N/D | 2/4 | (50%) | |
| | − | 2/11 | (18%) | P = 0.01 |
| | + | 6/11 | (55%) | |
| | ++ | 8/12 | (67%) | |
| ER/PR | −/− | 0/5 | (0%) | |
| | +/−, −/++, +/+, ++/− | 3/12 | (25%) | P = 0.0002 |
| | +/++, ++/+, ++/++ | 13/17 | (77%) | |
| TOTAL | | 18/38 | (47%) | |

*Receptor content 0-19 (−), 20-99 (+), or ≧100 (++) fmol/mg protein cytosol; N/D = not determined.
ER-ERE$_a$ = 0-49% (−) or 50-100% (+) of total anti-ER antibody recognized DNA complexes.
Significance test for linear trend in proportions and, Z-test p-values are according to Statistical Methods, 246-248 (1967) Iowa State University Press.

Table 2 illustrates prevalence of DNA binding ER a isoform in breast tumors of varying estrogen or progesterone receptor content.

In Table 2, 38 cancer tissue samples were tested for their ER-ERE complex formation and such formation was correlated to the level of the receptor content. Receptor content, expressed in fmol/mg protein cytosol was designated as follows: low (−) had 0-19 fmol/mg; moderate (+) had 20-99 fmol/mg; and high (++) had over 100 fmol/mg of protein. The breast cancer tissue samples were reprocessed as described above, their receptors were identified and receptor content was determined. The results are shown in column designated ER-EREa where the score of samples possessing intact DNA binding ER is shown on the left side and is correlated with total samples examined. Thus, where ER content was low, none of the six samples formed any ER-ERE complexes. When the level of ER content was moderate, 43%, or 6 from 14 samples, formed ER-EREa complex. In high level group, 67% of all samples, i.e. 12 out of 18 samples formed ER-EREa complexes.

In PR group, in low level group, 2 out of 11 samples, or about 18% of all samples formed ER-EREa complexes. In moderate level group, 6 out of 11 samples, i.e., 55%, and in high level group 8 out of 12, i.e. 67%, of all samples formed ER-ERE complexes.

In the group where both ER/PR contents were low, none of the 5 samples formed ER-EREa complexes. Three out of 12 samples in moderate level group, i.e., 25%, and 13 out of 17 samples in high level receptor content group, i.e., 77% samples ER-EREa complexes.

Protease inhibited sample extracts seen in FIG. 3 were scored by gel-shift assay as positive only if ER-ERE isoform a represented the most abundant form in levels equal to or larger than 50% of the total DNA bound ER such as seen in samples 187 and 226. Sample 88 with a total lack of DNA binding ER or sample 1222 producing only a minor component, i.e., less than 50% of ER-ERE isoform a were scored as negative. Of the 6 ER(−) negative samples containing 0-19 fmol/mg protein that were analyzed, all scored negative for intact DNA binding ER. That included one ER−/PR++ sample that possessed a DNA binding protein with preferred affinity for EREm unreactive to anti-ER antibodies, which finding was consistent with its content of more than 100 fmol PR/mg protein. Of the remaining 32 ER+tumor extracts, 18 (56%) scored positive for abundant ER-ERE isoform a.

Table 2 shows that intact DNA binding ER was detected in two-thirds of tumors containing high ER or PR content of more than 100 fmol/mg protein, but was not found in the majority of tumors with either low-to-moderate ER content of 20-99 fmol/mg protein, or absent PR content regardless of ER level. The abundance of ER-ERE isoform a correlated significantly with degree of significance for ER equal to p=0.002, for PR equal to p=0.01, and for combined ER/PR equal to p=0.0002 content.

Thus, analysis of nearly 40 primary breast cancers showed that some tumors containing abundant immunoreactive ER failed to demonstrate any DNA binding ER. In many other ER-positive tumors, the fraction of DNA which binds ER, i.e., isoform a, was low and consisted primarily of truncated receptor forms isoforms b or d which on Western analysis were revealed to be 50 kDa homodimers (isoform d) and 67 kD-50 kDa ER heterodimers (isoform b). Experiments using protease inhibitors (PI) and the demonstration of nuclear-localizing ER and ERE-binding COUP protein in these tumors indicated that the truncated forms, producing isoforms b and d of ER were likely to be present in vivo.

The differential susceptibility of specific ER domains to endoproteolytic cleavage has long been recognized and accounts for the ligand binding meroreceptors (3S) that are often isolated along with intact (4-8S) ER from estrogen responsive tissues. One such steroid-inducible protease activity has been found in normal reproductive tissues and leads to n-terminally truncated nuclear-localizing ER ($\sim$50 kDa), suggesting that there may be a physiological role for this form of post-translational ER modification (*Endocrinology*, 123:2548 (1988)).

The finding of endogenously cleaved 67 kDa ER and a $\sim$50 kDa nuclear receptor product may explain the occurrence of hormonally independent breast cancers, i.e. nonresponsive to hormonal treatments in some murine models. This led to suggestions that these truncated ER as well as other steroid receptors, may compete for available target gene response elements, may interfere with regulated gene transcription, and essentially become dominant-acting oncogenes (*Cancer Res.*, 50:451 (1990).

In the development of the current invention, using a gel-shift assay to detect DNA binding ER (ER-ERE) from extracts of human breast tumors, as described above, three a, b, and d ER-ERE isoforms that are distinguishable by size, electrical charge and mobility differences on non-denaturing gels were identified. Further analysis revealed that the b (mix of 67 kD and 50 kD) and d (50 kD) isoforms result from truncated tumor receptor binding to ERE. The total amount of DNA binding ER from many of these tumors was found to be less than the total level of immunoreactive ER. Indeed, some tumors with abundant immunoreactive ER having more than 50 fmol/mg of protein failed to produce any ER-ERE isoforms suggesting that all present ER were nonfunctional and lacked DNA binding capability. In all, the relative abundance of ER-ERE isoform a correlates well with the total amount of immunoreactive receptor (ER and PR) and with the expected incidence of responsiveness to hormonal treatment.

Stringent assay conditions were developed to eliminate non-specific DNA binding with proteins present in the high-salt extracts of both primary tumor samples and cultured tumor cells to assure the assay specificity. The DNA affinity and specificity in the new assay was first established by comparing ER complexes formed with a synthetic 35-mer sequence, as described above, containing either the ERE consensus sequence (5'GGTCACAGTGACC-3''), or a base substituted mutant EREM sequence (5'GGACACAGTGTCC-3'). The 35-mer sequence is known to preferentially bind to progesterone (PR), androgen (AR) or glucocorticoid receptors (GR). Since thyroid hormone receptors (THR), retinoic acid receptors (RAR), estrogen receptors (ER), and the recently cloned transcriptional factor known as COUP all possess near equivalent ERE binding and specificity and are found in human tissue samples, antibodies to ER and COUP were used to confirm the identify of these proteins in the gel-shifted DNA complexes.

Two different consensus sequences recognized with high affinity by THR, RAR and COUP receptors but with less affinity by ER were used to check for cross-binding by these receptors. The duplexed 32-mer consensus sequence for THR and RAR binding was GTCCAAAGTCAGGTCATGACCTGATCAAAG-TT, and the duplexed consensus sequence 28-mer used for COUP binding was TCTATGGTGTCAAAGGT-CAAACTTCTGA.

Cell lines including MCF-7 human breast cancer cells which are ER-positive, Chinese hamster ovary cells (CHO$^{ER}$) bearing recombinant and over expressing human ER receptors (as developed by P. Kushner of University of California San Francisco), and several other ER-negative cell lines were used as controls to develop the optimal gel-shift assay conditions necessary to detect ER-ERE isoforms from human breast tumors.

The whole-cell or tumor extracts containing ER were prepared according to the technique described in Example 2. To prevent nonspecific binding to ERE, the tissue extracts were incubated with excess poly [d(I-C)]and with unlabelled nonspecific single-stranded 20-mer mix having sequences 5'GAAGCT-GAGATTCCCCTCCA 3'; and 5'GGCTTGGGATG-GAGTAGGAT 3', added in 1:1 ratio, to improve the stringency of the binding conditions between ER and ERE.

The binding reaction between ER and ERE was performed with paired ER-containing extracts to $^{32}$P-radjolabelled ERE and/or confirmed with addition of the antibody, such as H222, H226, D27 anti-COUP or other specific antibody, to the tissue mixture before or in lieu of the addition of labelled ERE. The antibody was found to cause the supershift of the ER-ERE complex such as seen for example in FIG. 1, lines 1, 2, 3 and FIG. 2A, lane 2. Resulting ER-ERE complexes were separated on a cross-linked non-denaturing gel, such as acrylamide-bisacrylamide or other commercially available gels, prepared according to procedures described in *Molecular Cloning*, A Laboratory Manual, Ed. J Sambrook et al, 2nd Ed., Cold Spring Harbor Laboratory Press (1989) using a suitable buffer, such as TBA, as a running buffer. The gel was autoradiographed for 20-40 hours, preferably until the free DNA runs through the gel completely and the presence of gel-retarded complexes and unbound ERE were determined a bands visible by autoradiography.

Detection and composition of DNA binding estrogen receptor ER-ERE isoforms are shown in FIG. 1. CHO$^{ER}$ cells MCF-7 and cultured breast cancer cells both described above, were used as positive control samples for assays of an ER-Containing whole-cell extracts from a primary breast tumor (E), tested in this assay. Extracts from these cells, either alone or in case, of CHO$^{ER}$ in combination with cell extracts E with the addition of protease inhibitor (CHO$^{ER}$ E/PI) or in the absence of protease inhibitor (CHO$^{ER}$ +E) were incubated with $^{32}$P-labelled DNA (ERE). These extracts produced gel-shifted DNA-protein complexes a, b, c and d which are distinguishable by radiography from free unbound DNA shown as band F.

The results of the CHO$^{ER}$ cell extracts separations are shown in FIG. 1A, lanes 1-4. The results of the MCF-7 cell extracts separations are shown in lanes 10-13. The results of the breast tumor extracts E are shown in lane 9 and also in lanes 5-8. The combination of E+CHO$^{ER}$ in the presence of protease inhibitors is shown in lane 8. Gel-shift analysis of purified 67 kDa ER, derived from a human ER cDNA transfected Chinese hamster ovary cell line (CHO$^{ER}$), expressing $\geq 10^6$ ER molecules per cell, which produces a single gel retarded band referred to as isoform a, is shown in FIG. 1A, lane 1. Co-incubation of this positive control sample with anti-ER monoclonal antibody H226, H222, or D75 causes a supershift of isoform a, consistent with the increased size of the antibody bound ER-ERE complex as seen in FIG. 1A, lanes 2, 3, and 4, respectively.

FIG. 1A, lane 10 illustrates the more complex gel-shift pattern derived from whole-cell extracts of MCF-7 human breast cancer cells, containing more than $2 \times 10^4$ ER molecules per cell. MCF-7 extracts FIG. 1A, lane 10 produce a broad gel-shifted band composed predominantly of the ER-ERE isoform a recognized by both D75 and H226, lanes 11 and 12, and an abundant COUP-ERE complex, lane 13, having mobility similar to the ER-ERE isoform b that is recognized by the highly specific anti-COUP antibody lane 13. In these studies, it was found that gel-shift analysis detects as little as 0.1 fmol of DNA bound ER from whole-cell extracts containing 50 μg of total protein.

In FIG. 1A, lane 5, the gel-retarded ERE bound complex of sample E+CHO$^{ER}$ is resolved in into at least three components or three ER-ERE isoforms a, b and d. The presence of ER in these components is confirmed by coincubating the extract E+CHO$^{ER}$ with ER specific antibodies such as H226 (lane 7) and D75 (lane 6). The identity of these isomers and their relative amounts differ among various tumor tissues.

To assess the ability to arrest proteases that are activated during extraction of ER from tumors, tumor sample was used to prepare extract E, representative of tumors with high protease content was re-extracted in the presence of protease inhibitors (PI) and assayed again for DNA binding ER, FIG. 1A lane 3. The protease-active sample, produced only gel-shifted complex c, a single band seen with other unprotected tumor extracts and not recognized by any of the anti-ER monoclonal antibodies. In contrast, the protease-arrested E$^{PI}$ sample, not shown, containing near equivalent amount of immunoreactive ER, produced abundant gel-shifted ER-ERE complexes recognized by D75, with 50% of the total DNA binding ER identifiable as isoform a. Thus,, adding protease inhibitors at the time of tumor extraction appears necessary and sufficient to isolate intact, DNA binding ER from breast tumors, even those enriched in protease activity.

In summary, in FIG. 1A, $^{32}$P-labelled DNA (ERE) incubated with either recombinant human ER, purified from a cDNA transfected Chinese hamster ovary cell line (CHO$^{32}$) or ER-containing whole-cell extracts from a primary breast tumor (E) or cultured breast cancer cells (MCF-7), produced gel-shifted DNA-protein complexes bands a, b, c and d distinguishable after autoradiography from the free unbound DNA band (F). In the presence of co-incubated anti-ER monoclonal antibodies H226, H222, or D75, or a polyclonal antibody against the COUP transcription factor, the gel-shifted DNA-complexes containing either ER-ERE isoforms a and b, and d or COUP-ERE were supershifted due to the additional size of the antibody complex. CHO$^{ER}$ produced only ER-ERE isoform a. MCF-7 cells produced predominantly ER-ERE isoform a with substantial COUP-ERE. Extract E produced only ER-ERE complex c. Extract E$^{PI}$, not shown was prepared similarly from tumor sample E, except that protease inhibitors (PI) were added prior to tissue homogenization, produced isoforms a, b and d. When one-tenth volume of extract E was preincubated briefly with CHO$^{ER}$ (lane 5) isoforms b and d were formed along with a proportional loss in isoform a. The isoform a altering activity in extract E was completely prevented by the addition of protease inhibitors. Antibody D75 caused a supershift of ER-ERE isoforms a, b (partial), and d; H226 only supershifted isoform a. None of the anti-ER antibodies seemed to recognize complex c.

Figure 1B:
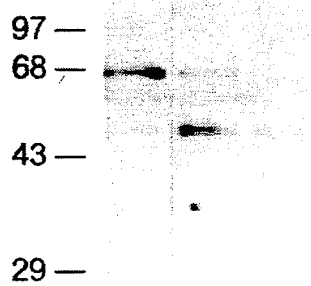

In FIG. 1B, gel-shifted ER-ERE isoforms a, b, and d derived from CHO$^{ER}$ were individually cut from the gel FIG. 1A, lane 1, denatured, reduced and analyzed by standard Western-blot technique using H222 antibody to reveal their ER composition. Prestained protein markers of molecular weight 29, 43, 68 and 97 were obtained from GIBCO/BRL.

To determine the molecular composition of ER present in isoforms b and d, the CHO$^{ER}$ sample was preincubated with breast cancer tissue extract E, gel-shifted, and the isoform bands excised and subjected to Western analysis according to Example 2. FIG. 1B demonstrates that isoform a contains primarily 67 kDa ER, while isoform b and d isoforms contain truncated 50 kDa ER present as ERE bound heterodimers and homodimers, respectively, The 67 kDa and 50 kDa ER are recognized by either H222, D75, or H226 monoclonals antibodies on Western analysis, suggesting that the loss of b and d isoform recognition by H226 on gel-shift analysis is due to altered receptor conformation under non-denaturing assay conditions. These findings indicate that a proteolytic activity present in some breast tumor extracts can impair the gel-shift detection of DNA binding ER.

The FIG. 2 illustrates DNA binding and nonbinding immunoreactive ER from representative breast tumor samples.

Extracts seen in FIG. 2 are prepared according to procedure described in Example 2. The extracts, containing more than 50 fmol ER/mg protein from three primary breast tumor designated 1222, 226 and, 88 were freshly prepared in the presence (+) or absence (−) of protease inhibitors (PI) and used for both gel-shift assays FIGS. 2A and C and Western immune-blotting FIG. 2B and C. Samples 1222 (+) and 226 (+) contained 0.55 fmol ER per lane, 1222 (−) and 226 (−) contained 0.74 fmol ER per lane, 88 (+) and 88 (−) contained 0.30 fmol ER and 0.40 fmol ER per lane, respectively.

In FIG. 2A. gel-shift assays were performed as described in FIG. 1 for the identification of DNA bound complexes a, b, c and d. Anti-ER monoclonal antibody D75 was used to confirm the finding of ER-ERE isoforms in 1222(+), 226(+) and 226(−), that were not found in 1222(−) 88(+) or 88(−).

In FIG. 2C, tumor extracts 88(+) and 226(+), along with control samples E, CHO$^{ER}$ +E, and MCF-7 which were described in FIG. 1, were gel-shifted using unlabelled ERE according to Step 2, Example 3 with subsequent Western-blot transfer of the proteins to membranes hybridized with anti-ER monoclonal H222 antibody, detected by rabbit anti-rat IgG and $^{125}$I-Protein A (100 μCi/μg; from NEN Dupont, Wilmington; DE). The probed membrane was divided along the dotted line and variable autoradiograph exposures of the lower portion of this gel-shift Western blot show DNA bound ER as either isoforms a, b, or d identified by using 32P-labelled ERE in parallel lanes, from 226+(lane 2) and MCF-7 (lane 5) samples (4 day exposures), from the combination of CHO$^{ER}$+E (lane 4), after 15 hours exposure, but not from samples 88 (+)(lane 1) or E (lane 3), after 4 day exposures. Unbound ER was detected in the upper portion of the blot as a more slowly migrating protein band that was present in 88(+), 226(+), and E, (Upper lanes 2 and 3) but not in MCF-7 (lane 5) or pure CHO$^{ER}$ after 3 hours exposure.

In FIG. 2B, a standard Western-blot detection of ER with H222 antibody was performed from sodium dodecyl sulfate (SDS)- polyacrylamide (10%) gels after samples were boiled in SDS (1%) and DTT (100MM). The relative proportions of intact (67 kDa) and truncated ($\leq$50 kDa) immunoreactive ER are shown for the control (lanes 1 and 2) and tumor (lanes 3-8) extracts prepared in the presence (+) or absence (−) of protease inhibitors. Prestained protein 29, 43, 68 and 97 molecular weight markers are shown on the left side.

In FIG. 2, comparison is made of ER-ERE formation from receptor-positive tumor extracts having 20 or more fmol/ER/mg total protein, prepared in the presence or absence of protease inhibitor. The three representative samples, 1222, 226 and 88 shown in FIG. 2A illustrate the changes in isoform profiles a, b and d that can result from ER proteolysis occurring during tissue processing and during the brief incubation step prior to gel electrophoresis. Each of these isoforms have slightly different gel mobilities, based on size and electrical charge. These altered isoform profiles occurred without significant changes in total level of immunoreactive ER, as routinely measured by using two different c-terminal anti-ER monoclonal antibodies D57 and H222. In tumor sample 1222, the ex vivo proteolysis was minor, converting isoform a predominantly present into isoforms b and d along with isoform c complex. In a third sample 88, the ex vivo proteolysis enhanced the amount of pre-existing c complex but none of the gel-shifted protein complex was recognizable by any of the used anti-ER monoclonal antibodies D75, H222, or H226, even in the presence of protease inhibitor.

FIG. 2B illustrates results obtained from Western blot assay. Western blot assay of the same sample extracts as used in FIG. 2A was performed using H222 and H226 antibody. The assay detected varying amounts of 67 kDa, 50 kDa, and some lower molecular weight ER bands, as shown in FIG. 2B. In some samples, for example, in sample 1222, the ex vivo proteolytic loss of 67 kDa ER, with most 50 kDa ER remaining, was particularly evident in FIG. 2B, lane 4. In other samples, the Western data suggested that either partial proteolysis, as seen in sample 226, lane 6 or essentially complete proteolysis in sample 88, lane 8 of 67 kDa ER to truncated 50 kDa ER had occurred either in vivo or before tissue processing. The failure of some tumor extracts, such as proteolyzed sample 1222, lane 4 and protease-arrested sample 88, lane 7, to form any gel-shifted ER-ERE isoforms was surprising since they contained abundant immunoreactive 50 kDa ERE which should possess an intact, although possibly modified, DNA binding domain enabling the formation of isoform d.

To demonstrate directly the abundance of non-DNA binding ER present in these sample extracts, the gel-shifts were run as before using unlabelled instead of $^{32}$P-labelled ERE, electroblotted and probed as Western-style immunobolts using the H222 antibody. The results are illustrated in FIG. 2C. The observations derived from these gel-shift Western blots was that primary tumor extracts contained non-DNA binding ER that migrated more slowly than DNA bound ER, consistent with the mildly acidic isoelectric pH of intact and truncated ER. This non-DNA binding ER was present in amounts inversely related to the proportion of ER-ERE isoform a. It appears that the lack of DNA binding by estrogen receptors present in tumors results from some protease-independent mechanism in as much as MCF-7, lane 5 and CHO$^{ER}$, lane 4 samples produced no unbound ER on gelshift Western blot assay even with proteolytic pretreatment, as shown in FIG. 2C. The level of non-DNA binding ER in tumor extracts was unchanged in each of the sample extracts analyzed for FIG. 2C. There is no obvious explanation to account for the apparently greater immunoreactivity of unbound ER over that present in the ER-ERE isoforms.

FIG. 3 shows intact DNA binding COUP protein and immunohistochemical preservation of ER in tumors with abnormal DNA-binding ER.

Extracts 1222 and 88, FIG. 3 lanes 1–4 and 5–8, together with extracts 187 and 240, lanes 9–12 and 13 and 14 from other primary tumor samples, were prepared as described in Example 2, in the presence (+) lanes 1, 2, 5, 6, 9–14, and absence (−) lanes 3, 4, 7 and 8 of protease inhibitors. These extracts either alone or in the presence of polyclonal antibody DNA-binding COUP, lanes 2, 4, 6, 8 and 12, or anti-ER monoclonal antibodies D75, lanes 10 and 14, or H226, lane 11, recalled protein-DNA complexes that were supershifted by both COUP and D75 or H226. DNA binding COUP was detected in all samples containing protease inhibitor but not in those where there was no protease inhibition present. Sample 240 which did not contain the usual ER-ERE isoforms a, b, c and d, contained a higher migrating complex that was supershifted by anti-ER monoclonal antibody D75.

In studies shown in FIG. 3, COUP polypeptide binding to ERE and checked immunohistological localization of ER in residual portions of the frozen tissue samples were measured to determine if receptor degradation might have occurred after surgical resection despite immediate tissue cryopreservation at −70° C. and before protease-arrest during extract preparation.

Figure 3A:
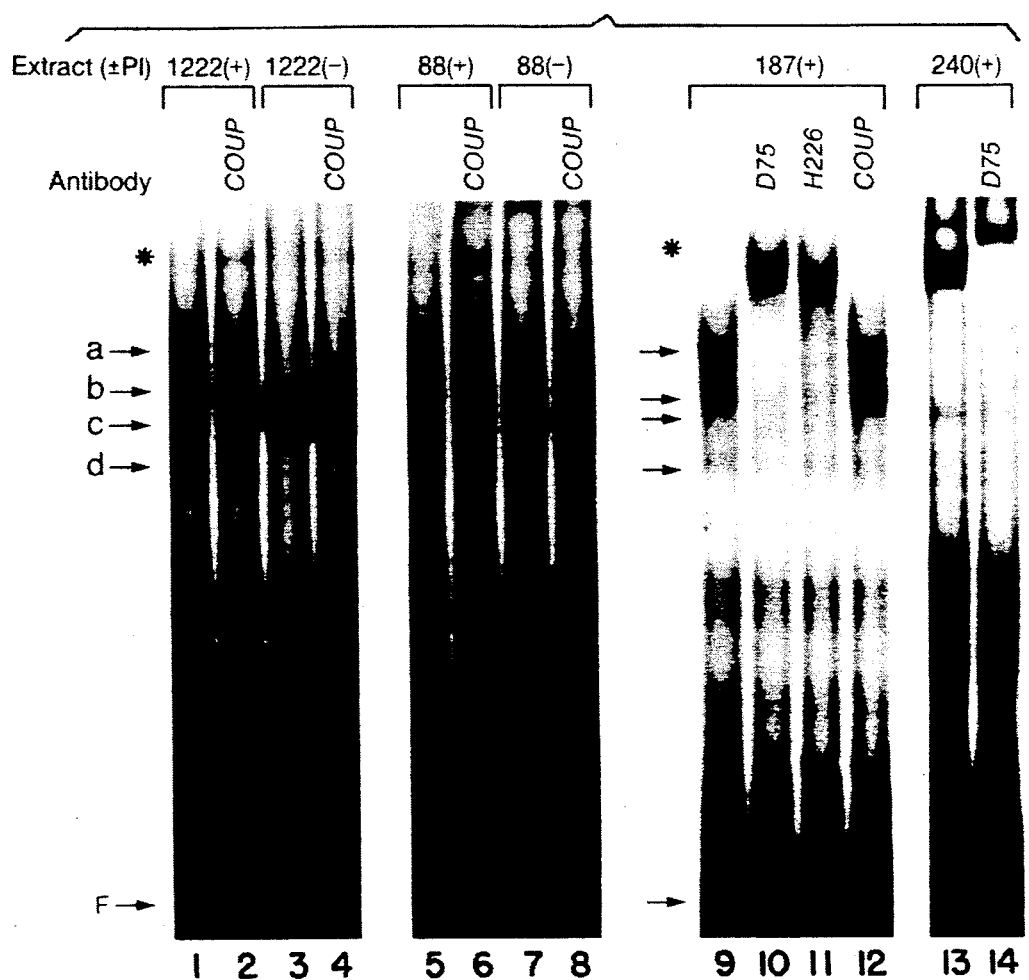
FIG. 3A and 3B depict intact DNA binding COUP protein as a part of the total cell proteins that bind ERE including ER, and immunohistochemical preservation of ER in tumors with abnormal DNA-binding ER.
Figure 3B:
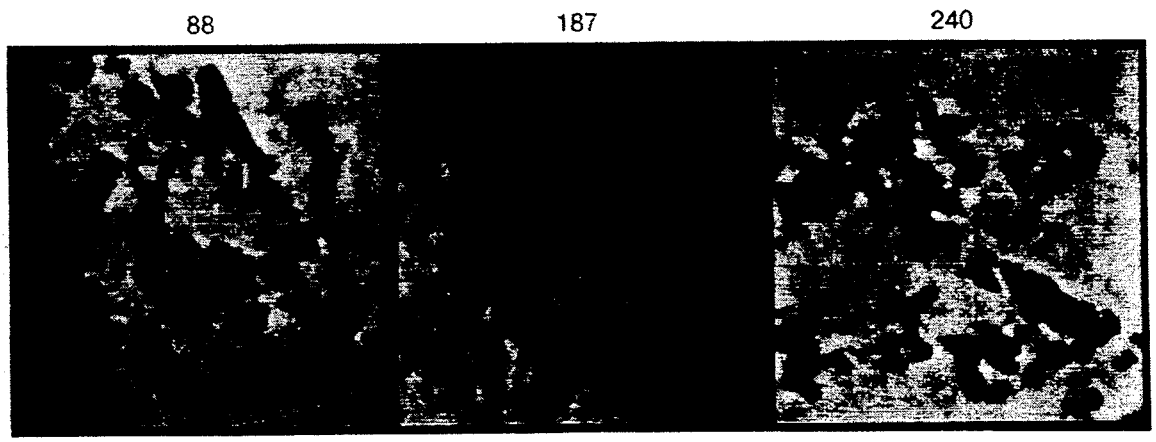

FIG. 3A shows that tumor samples 1222 and 88, extracted in the absence of protease inhibitors formed no detectable COUP-ERE complexes while the same samples processed in the presence of protease inhibitors possessed comparable levels of ERE-binding COUP polypeptide. These results indicate that COUP, like ER, is susceptible to ex vivo proteolytic degradation. Therefore, the lack of 67 kDa ER and inability to form ER-ERE isoform a from protease-arrested extracts containing intact DNA binding COUP, samples 1222 and 88, shown in lanes 2 and 6, likely reflects the in vivo state of these tumors. The excellent cytological preservation and the presence of nuclear-localizing ER in these samples as shown in FIG. 3B also confirmed that these tumors were adequately cryopreserved and did not suffer from significant ex vivo cellular degradation following surgical excision.

The ER-ERE isoform profiles shown for the protease-inhibited extracts from tumors 1222, FIG. 2A, lane 1 and FIG. 3A, lane 2, 226, FIG. 2A, lane 5, and 187, FIG. 3A, lane 9 are representative of virtually all the receptor-positive breast tumors which were analyzed. Samples with complete absence of immunoreactive DNA binding ER, such as sample 88, FIG. 3, lane 5, and FIG. 3, lane 9, were uncommon but not rare. Only tumor extract 240, FIG. 3, lane 13, produced an abnormally large (more slowly migrating) ER-ERE complex. Western blotting of this extract demonstrated immunoreactive ER of size smaller or equal to 67 kDA. The markedly gel-shifted complex from this nuclear-localizing ER was susceptible to proteolysis, not disaggregated by RNase, unreactive to various heat-shock antibodies, and not evident on incubation with EREM instead of ERE.

Since the absolute content of tumor ER and PR are each considered to be predictors of clinical response to antiestrogen therapy, all gel-shift scores studied here were correlated with receptor levels measured independently by commercial immunoassay kits available from Abbott Labs on contiguous portions of the same tumors.

UTILITY

Most patients with breast cancer are treated with either chemotherapy or antiestrogenic agents. According to current beliefs restated in *J. Clin. Oncol.*, 8:1025 (1990), the likelihood that a breast tumor will respond to antiestrogen therapy depends on the level of estrogen receptor in the tumor, as measured by radioligand binding or immunochemical assay. Together with ER, progesterone receptor (PR) content is also usually determined because it provides some indication that the ER in the tumor are functional and capable of inducing synthesis of PR (*Semin. Oncol.*, 10:2 (1983)), although examples of breast cancers that express only PR independent on the presence of ER are well known. (*Cancer Res.*, 46:1124 (1986)).

Unfortunately, currently 20-30% of ER+/PR+ tumors, and up to 60-70% of ER+/PR− tumors fail to respond to antiestrogenic therapy for reasons that are very poorly understood. It has been recently suggested that these endocrine-resistant tumors contain dysfunctional ER (*Cytometry*, 11:359 (1990)).

Since the early identification of such endocrine-resistant tumors would allow patients to be started on alternative forms of therapy, many investigators have been trying to develop assays to detect such dysfunctional ER (*Science*, 189:726 (1975); *Mol. Endo.*, 3:22 (1989); *Oncogene* 4:1037 (1989)).

Most recently, gel-shift assays described in *Mol. Cell. Biol.*, 9:43 (1989) became available and have provided a sensitive means of assaying relatively pure receptor proteins for high affinity, high specificity DNA binding. However, these assays have not been suitable for and have not been applied to the functional assessment of receptor content from extracts of primary breast tumors.

Gel-shift assay have until now provided a sensitive means of assaying relatively pure receptor proteins for high affinity, high specificity DNA binding but have never been, before this discovery, applied to the functional assessment of ER from extracts obtained from human cancer tissue and ultimately for prediction of responsiveness of such cancer to certain treatments.

The findings of endogenously cleaved 67 kDa ER and a ~50 kDa nuclear receptor products may also explain progression to hormonally independent breast cancers in some murine models and has led investigators to suggest that truncated ER as well as other steroid receptors may compete for available target gene response elements, interfere with regulated gene transcription, and essentially become dominant-acting oncogenes.

Using a modified gel-shift Western blot assay to detect DNA binding ER as ER-ERE complexes from extracts of human breast tumors, three ER-ERE isoforms a, b, and d were identified that are distinguishable by mobility differences on non-denaturing gels. Moreover, isoform c ER-ERE complex was found of which function is not quite clear. Analysis of these samples reveals that the b and d isoforms result from truncated tumor receptor binding to ERE and that the isoform a represent the intact ER-ERE complex and is an evidence of fully functional ER.

However, the total amount of DNA binding ER from many of these tumors was found to be less than the total immunoreactive ER. Indeed, some tumors with high levels of immunoreactive ER of more than 50 fmol/mg protein failed to produce any ER-ERE isoforms. In all, the relative abundance of ER-ERE isoform a correlates well with the total amount of immunoreactive receptors (ER and PR) and the expected incidence of endocrine responsiveness.

The new gel-shift Western blot assay thus enables determination of various ER-ERE isoforms, their quantitation and the degree of their activation. Correlation of the presence of certain ER-ERE isoforms with their amount will allow prediction of responsiveness of the tumor tissue to the treatment with hormones.

The abundance of isoform a evidences the presence of high level of functional ER receptors and predict their positive response to hormonal treatment.

The presence of isoform b would evidence the presence of mixture of functional and nonfunctional receptors. Presence of isoform d would evidence primarily the presence of nonfunctional ER. Thus, if the level of isoform a is higher than level of combined b and d, the tumor will respond to hormonal treatment. If, on the other hand, the isoforms b and d are in higher level than isoform a, the tumor would not respond to hormonal treatment.

Similarly, if there is high level of free ER present, such presence evidence nonfunctional receptors and would be interpreted so that the tumor will not respond to hormonal treatment.

Using different DNA binding sequences specific for each member of the steroid receptor gene family such as ER, PR, androgen receptor (AR), glucocorticoid receptor (GR), THR, etc., such DNA binding receptor isoforms can be measured from various normal tissues or tumors, such as for example breast, endometrial, ovarian and prostatic tissues.

In this respect, this assay and method is also applicable in prognosis of other cancers than breast cancers.

Furthermore, the new gel-shift assays may be easily modified to avoid the use of $^{32}P$ (or other radionuclides) by established techniques by simply synthesizing DNA elements with modified bases (eg. avidin-linked) that can be measured by other sensitive binding or enzyme-mediated spectrophotometric assays, more acceptable to commercial labs. Unlabelled ERE can also be coupled to sepharose beads to isolate ER-ERE complexes which can be quantitated by commercially available peroxidase-anti ER spectrophotometric assays available from Abbott Labs. Other solution-based vs. gel-based assays can be developed to avoid gel electrophoresis and to quantitate total receptor-bound DNA complexes. These complexes, however, would require secondary analyses to distinguish the various isoforms on the basis of size or charge, since individual isoforms may be clinically important if each is associated with a different prognosis.

These and other modifications of this method are intended to be encompassed within the scope of this invention.

EXAMPLE 1

Quantitation of ER-ERE Isoforms

This example illustrates the method of quantitating ER-ERE isoforms.

Whole-cells extracts were prepared using approximately 100-200 mg of wet tissue or tumor weight (or about $10^7$ cells). The carefully dissected fresh or cryopreserved tissue sample was washed with cold PBC, homogenized in binding buffer (20 mM Tris pH 7.5, 2 mM DDT, 20% v/v/ glycerol, 0.4 M KCl), centrifuged at $100,000 \times g \times 1$ hour at 2° C. The supernatant was collected, and protein content determined by Bradford assay. Extracts were aliquoted and cryopreservied at $-80°$ C. for later analysis. Thawed extract (10–30 ug) were incubated with 2 ug of poly [d(I-C)] dissolved in 100 mM KCl, 10 mM Tris pH 7.5, 2 mM DTT, 5% v/v of glycerol at 0° C. $\times$ 15 minutes to prevent some nonspecific binding to ERE. In addition, 1 pmol of unlabelled nonspecific 20-mer mix as described in the Example 2 was added to improve the stringency of the binding conditions between ER and ERE. The sequence of either the natural ERE or the mutant EREM is shown in Example 2. The binding reaction was performed with paired ER-containing extracts to either radiolabelled ERE or EREm initiated by addition of $[^{32}P]5'$ end-labelled ERE (or EREm) oligomer (5 fmol, $4 \times 10^4$ cpm) incubated at 20° C. $\times$ 30 minutes in a final volume of 20 ul. Complexes ER-ERE or ER-EREm were separated on a 4% loosely cross-linked (acrylamide/bisacrylamide=30/1) non-denaturing gel using ($0.5 \times$) TBE as a running buffer which was autoradiographed to reveal gel-retarded complexed and free (F) bands containing ERE or EREM. Corresponding bands of ER-ERE or ER-EREm were identified on autoradiographs, quantitated by densitometric scanning, and subtracted ([ER-ERE]−[ER-EREm]$_i$) to yield the amount and type of each specific ER-ERE isoform a, b, and d.

EXAMPLE 2

Detection and Composition of DNA Binding Estrogen Receptors

This example illustrates detection and composition of DNA binding estrogen receptor ER-ERE isoforms.

Cell nuclei were isolated from CHO$^{ER}$ cells according to procedure described in Cell, 56:335 (1989) by douncing the cells in 0.25M sucrose and pelleted twice through 1.7M sucrose cushions, then suspending then in a nuclear lysis buffer, homogenized, and the semi-purified ER extract were prepared by ammonium sulfate precipitation and dialysis, as described in Cell 47:767 (1986).

Whole-cell extracts were prepared using approximately 100-200 mg of wet tumor weight or $10^7$ cultured cells. Carefully dissected fresh or cryopreserved tumor samples were pulverized to powder at liquid nitrogen temperature using a Bessman tissue pulverizer (Fisher Scientific), placed into ice-cold extraction buffer (20 MM Tris pH 7.5, 10 mM DDT, 20% v/v glycerol, 0.4 M KCl), either without or with protease inhibitor leupeptin (0.5 μg/ml), phenylmethanesulfonyl fluoride (2 mM), or antipain (10 μg/m), all obtained from Boehringer Mannheim. The samples were solubilized and homogenized by Polytron (Brinkmann). The extract was then centrifuged at 100,000 g $\times$ 20 minutes at 2° C., the was supernatant collected, ER content was determined using ER-EIA, assay from Abbot (North Chicago, IL) and total protein content was determined by Bradford Assay from Bio-Rad. Extracts were aliquoted and cryopreserved at $-80°$ C. for later analysis. Thawed extracts in 10–50 μg total protein quantities were incubated with 2 μg poly[d(I-C)] obtained from Boehringer Mannheim, (Indianapolis, IN), in 100 mM KCl, 10 mM Tris pH 7.5, 20 mM Tris pH 7.5, 2 mM DTT and, 5% v/v glycerol at 0° C. $\times$ 15 minutes. In addition, 10 pmol of unlabelled nonspecific 20-mer mix having a sequence shown below, was added to increase the stringency of the binding conditions between ER and ERE. The binding reaction was initiated by adding 10 fmol ($4 \times 10^4$ cpm) of $[^{32}P]5'$ end-labelled duplexed ERE oligomers having a sequence shown below. The mix was incubated at 20° C. $\times$ 30 minutes in a final volume of 20 μl. The excess molar amount of ERE relative to ER in these reaction conditions was set to produce virtually complete ER-ERE formation given the $K_d$ for this complex $\simeq 10^{-9}$ M as described in Cell, 60:953 (1990). Complexes were separated on a 4% loosely cross-linked (acrylamide/bisacrylamide=30:1) non-denaturing gel using $0.5 \times$ TBE (50 mM Tris-50 mM boric acid-lmM EDTA) as running buffer. Gels were dried and autoradiographed to reveal complexed a, b, c and d or free (F) bands.

To confirm the protein bound within complexes, 0.05 mg of antibody was added to the incubation mix to observe supershifting of the complexes.

Synthetic duplexed and single-stranded DNA oligomer used for this procedure was:

duplexed ERE:
  5'GTCCAAAGTCAGGTCACAGTGACCT-
  GATCAAAGTT 3' and single-stranded 20-mers were:

5'GAAGCTGAGATTCCCCTCCA 3'

5'GGCTTGGGATGGAGTAGGAT 3'.

The results were already described in general in the specification and are illustrated in FIGS. 1, 2 and 3.

EXAMPLE 3

Two-Stejo Gel-Shift Western Blot Assay

This example illustrates the procedure used in the two-step gel-shift Western blot assay. The first step separates the free-unbound DNA from DNA ER-ERE complexes and determines the quality of bound ER-ERE complexes. The second step determines and measures the amount of unbound ER in the sample.

Materials and Preparations

Extraction Buffer Composition 20 mM Tris pH 7.5, 10 mM DDT, 20% v/v glycerol, 0.4 M KCl, 0.5 μg/ml protease inhibitor leupeptin, 2mM phenylmethanesulfonyl fluoride, and 10 μg/m antipain, all obtained from Boehringer Mannheim.

Incubation Buffer

Poly[d(I-C)]obtained from Boehringer Mannheim, Indianapolis, IN, and unlabelled nonspecific 20-mer having a sequence 5'GAAGCTGAGATTCCCCT-CCA 3' and 5'GGCTTGGGATGGAGTAGGAT 3',as 1:1 mix is dissolved 20 mM Tris pH 7.5, and 2 mM DTT to a final concentration of 0.15 μg/μl and 0.15 pmol/μl respectively. Single stranded 20-mer is added to increase the stringency of the binding conditions between ER and ERE.

Radiolabelled ERE [$^{32}$P]5' end-labelled duplexed ERE oligomer having a sequence
5'GTCCAAAGTCAGGTCACAGTGACCTGAT-CAAAGTT 3' (10 fmol; $4 \cdot 10^4$ cpm).

Separation Gel

Separation gel is a 4% loosely cross-linked acrylamide/bisacrylamide (30:1) non-denaturing gel prepared according to procedure 6.36, described in *Molecular Cloning*, A Laboratory Manual, Ed. J Sambrook et al, 2nd Ed., Cold Spring Harbor Laboratory Press (1989).

Gel Running Buffer

Gel running buffer is 50 mM Tris-50 mM boric acid-1mM EDTA (TBA).

Preparation of the Tissue

Fresh or cryopreserved tumor samples (100–200 mg of wet tumor weight or $10^7$ cultured cells) are carefully dissected, placed at liquid nitrogen temperature and pulverized to powder using a Bessman tissue pulverizer from Fisher Scientific.

Assay Procedure—Step 1

1-1. The tissue powder is placed into 1.5 ml of ice-cold extraction buffer.

1-2. The samples are solubilized and homogenized by Polytron (Brinkmann) solubilizer.

1-3. The sample is centrifuged at 13,000–100,000 g×10–20 minutes at 4° C.

1-4. The supernatant is collected and the pellet is discarded.

1-5. ER content is determined using by using enzyme immunoassay commercially available as ER-EIA Assay from Abbott North Chicago, IL.

1-6. Total protein content is determined by Bradford Assay from Bio-Rad, Hercules, CA.

1-7. Extracts are aliquoted for testing and the remainder is cryopreserved at −80° C. for additional later analysis. 0 1-8. Two 5 μl samples of the extract each containing 10μ50 μg of total protein are added separately to 15 μl of incubation buffer and 0.05 μg of an antibody D75, H222 and H226 is added to the second sample to be run in parallel to the first sample without the antibody.

1-9. 10 fmol (4 ×$10^4$ cpm) of [$^{32}$P]5' end-labelled duplexed ERE oligomers are added to each sample to initiate the binding reaction.

1-10. The samples having a final volume of 20 μl are incubated at 20° C.×30 minutes to form ER-ERE complexes.

1-11. The samples containing ER-ERE complexes are applied to a well on a 4% loosely cross-linked non-denaturing 20 cm vertical gel and separated using 0.5 ×TBE as running buffer for 2-4 hours at 12 volts/cm.

1-12. Gels are dried onto Whatman 3 mm paper and autoradiographed and photographed to reveal formed ER-ERE complexes or free DNA bands.

1-13. Results are evaluated as ER-ERE complex bands a, b, c and d in each sample without the antibody and as the supershifted bands corresponding to ER-ERE a, b, or d bands produced in samples containing antibody. These gel-shifted and supershifted ER-ERE complexes are distinguishable after autoradiography or staining from the free unbound DNA (ERE) band which is running ahead of the ER-ERE complexes. In the presence of antibodies, the gel-shifted ER-ERE isoforms are further supershifted due to the additional size of the antibody complex. When the tissue extract produces predominantly ER-ERE isoform a, the sample is considered to be positive and will be evaluated as responding to hormonal treatment. When the sample contains no supershifted complexes or complexes b and d, the sample will be considered negative and not responsive to the hormonal treatment and the alternate therapy will be suggested.

Assay Procedure—Step 2

2-1. Tissue samples are processed as in Step 1, 1-1 through 1-8 and 1-10 and 1-11, except that samples will contain unlabelled ER rather than not labelled ERE.

2-2. The unbound ER and ER-ERE in the gel obtained in Step 1-11 is transferred to a nylon membrane.

2-3. The nylon membrane is soaked in the solution of labelled anti-ER antibody for 1 hour to allow binding of antibody to ER and ER-ERE complexes.

2-4. The membrane is washed with buffer to remove all unbound antibody.

2-5. The nylon membrane is autoradiographed and photographed.

2-6. Results are evaluated as the free unbound ER and ER-ERE complexes. ER-ERE a, b, c and d complexes position is compared with the position a, b, c and d complexes obtained in the Step 1.

We claim:

1. A method for determining the relative proportion of functional estrogen receptor in human tumor tissue, wherein functional estrogen receptor binds normally to estrogen responsive element, and wherein the relative proportion of functional receptor is correlated to responsiveness of the tumor tissue to hormonal treatment, said method comprising the steps of:

(a) contacting a first sample of the human tumor tissue with an anti-estrogen receptor antibody to determine the total amount of immunoreactive estrogen receptor in the human tumor tissue;

(b) contacting a second sample of the human tumor tissue with non-specific DNA oligomers in an amount sufficient to eliminate non-specific DNA binding;

(c) contacting the human tumor tissue sample of step (b) with end-labeled duplexed estrogen responsive element DNA oligomers;

(d) dividing the sample of step (c) into two parallel samples and incubating one with anti-estrogen receptor antibody;

(e) separating normal estrogen receptor-estrogen responsive element complexes from other complexes in each of the parallel samples of step(d) by gel shift assay, according to molecular weight;

(f) determining the proportion of normal estrogen receptor in the tumor tissue by measuring the amount of estrogen receptor which forms normal estrogen receptor-estrogen responsive element complexes and comparing it to the amount of immunoreactive estrogen receptor in the human tumor tissue; and (g) correlating the proportion of functional estrogen receptor in the tumor tissue with the responsiveness of the tumor tissue to hormonal treatment, wherein tumor tissue with 50% or more functional estrogen receptor is presumed to be responsive to hormonal treatment, while tumor tissue with less than 50% functional estrogen receptor is presumed to be non-responsive.

2. The method of claim 1 wherein the non-specific DNA oligomers are poly[d(I-C)], unlabeled nonspecific 20-mers having sequences 5'GAAGCTGAGATTCCCCTCCA 3' and 5'GGCTTGGGATGGAGTAGGAT 3'.

3. A method for determining the relative proportion of functional estrogen receptor in human breast cancer tissue, wherein functional estrogen receptor binds to estrogen responsive element to form isoform a, and wherein the relative proportion of functional receptor is correlated to responsiveness of the breast cancer tissue to hormonal treatment, said method comprising steps:

(a) contacting the breast cancer tissue with an extraction buffer;
(b) homogenizing the mixture of step (a);
(c) centrifuging a homogenate of step (b);
(d) separating an extraction supernatant from a pellet obtaining by centrifugation;
(e) preparing two parallel samples of the extraction supernatant obtained in step (d) and incubating these samples in an incubation buffer containing nonspecific DNA, wherein one sample is incubated in the presence of a specific estrogen receptor antibody and the second sample is incubated without the estrogen receptor antibody;
(f) adding to samples of step (e) labeled duplexed estrogen responsive element DNA oligomers;
(g) incubating the samples of step (f) to form estrogen receptor-estrogen responsive element complexes;
(h) separating estrogen receptor-estrogen responsive element complexes from non-specifically bound DNA complexes and from unbound estrogen responsive element DNA bands on gel;
(i) autoradiographing said gel;
(j) observing separation of estrogen receptor-estrogen responsive element complexes into estrogen receptor-estrogen responsive element bands corresponding to isoforms bands (a), (b), and (d);
(k) observing and comparing a supershift of estrogen receptor-estrogen responsive element complexes bands corresponding to isoforms (a), (b), or (d) in samples incubated in step (e) with the specific estrogen antibody with the estrogen receptor-estrogen responsive element complexes bands corresponding to isomers (a), (b), or (d) in samples incubated in step (e) without the specific estrogen receptor antibody;
(l) determining a relative level of the estrogen receptor-estrogen responsive element complex band corresponding to isomer (a) against estrogen receptor-estrogen responsive element complexes bands corresponding to isomers (b) and (d);

(m) wherein a level of isoform a higher than the combined levels of isoforms b and d is correlated with responsiveness of the breast cancer tissue to hormonal treatment, while combined levels of isoforms b and d higher than the level of isoform a is correlated with non-responsive of the breast cancer tissue to hormonal treatment.

4. The method of claim 3 wherein the incubation buffer consists essentially of poly[d(I-C)], unlabeled nonspecific 20-mer having sequences 5'GAAGCTGAGATTCCCCTCCA 3' and 5'GGCTTGGGATGGAGTAGGAT 3', and dTT.

5. An assay for determining the relative proportion of functional estrogen receptor in human tumor tissue, wherein functional estrogen receptor binds to estrogen responsive element to form isoform a, and wherein the relative proportion of functional receptor is correlated to responsiveness of the breast cancer tissue to hormonal treatment, said assay comprising steps:

(a) preparing an extraction buffer composition consisting essentially of 20 mM Tris having pH 7.5, 10 mM DTT, 20% v/v/ glycerol, 0.4 M KCL, 5 $\mu$g/ml protease inhibitor leupeptin, 2 mM phenylmethanesulfonyl fluoride, and 10 $\mu$g/m antipain;
(b) preparing an incubation buffer consisting essentially of poly[d(I-C)], and of unlabelled nonspecific 20-mer having a sequence 5'GAAGCTGAGATTCCCCTCCA 3' and 5'GGCTTGGGATGGAGTAGGAT 3', as 1:1 mix;
(c) preparing a radiolabelled [$^{32}$P]5' end-labelled duplexed estrogen responsive element oligomer having a sequence 5'GTCCAAAGTCAGGTCACAGTGACCTGATCAAAGTT 3';
(d) preparing a non-denaturing separation gel from 4% loosely cross-linked acrylamide/bisacrylamide in a ratio 30/1;
(e) preparing a gel running consisting essentially of 50 mM Tris, 50 mM boric acid and 1 mM EDTA;
(f) preparing a tumor tissue sample for assaying by freezing 100–200 mg by wet weight of tumor tissue and pulverizing it into a powder;
(g) dissolving the tissue powder of step (f) into 1.5 ml of ice-cold extraction buffer of step (a);
(h) solubilizing and homogenizing the dissolved sample of step (g) by a solubilizer;
(i) centrifuging the solubilized sample at 13,000–10,000 g for 10–20 minutes at 4° C.
(j) collecting the supernatant and determining amount of estrogen receptor by an enzyme immunoassay;
(k) determining the total protein content;
(l) preparing two samples of the supernatant each containing between 10–50 $\mu$g of total protein;
(m) adding one sample of step (1) to 15 $\mu$l of incubation buffer of step (b);
(n) adding the second sample to a mixture consisting of 15 $\mu$l of incubation buffer of step (b) and 0.05 $\mu$g of an estrogen receptor specific antibody;
(o) adding to each sample of steps (m) and (n) 10 fmol ($4 \times 10^4$ cpm) of [$^{32}$P]5' end-labelled duplexed estrogen responsive element oligomer of step (c);
(p) incubating samples of step (o) at 20° C. for 30 minutes;
(q) applying each sample of step (p) to a wall of the separation gel of step (d), wherein said gel is a 4% loosely cross-linked non-denaturing 20 cm vertical gel, and electrophoretically separating formed estrogen receptor-estrogen responsive element complexes bands corresponding to isoforms (a), (b), (c) from bands corresponding to free DNA and to non-specific DNA complexes, using gel running buffer of step (e) for 2-4 hours at 12 volts/cm;

(r) autoradiographing the gels;

(s) evaluating the samples of step (m) not containing antibody for presence of formed estrogen receptor-estrogen responsive element complexes corresponding to isoforms (a), (b), and (d) and comparing these complexes with estrogen receptor-estrogen responsive, element complexes present in samples of step (n) containing antibody, wherein the complexes present in samples containing antibody are supershifted due to the additional size of antibody;

(t) wherein a level of isoform a higher than the combined levels of isoforms b and d is correlated with responsiveness of the tumor tissue to hormonal treatment, while combined levels of isoforms b and d higher than the level of isoform a is correlated with non-responsiveness of the tumor tissue to hormonal treatment.

6. The assay of claim 4 wherein the incubation buffer consists essentially of poly[d(I-C)], unlabeled nonspecific 20mer having sequences 5'GAAGCTGAGATTCCCCTCCA 3' and 15'GGCTTGGGATGGAGTAGGAT 3', and dTT.

* * * * *